United States Patent [19]

Hachey et al.

[11] Patent Number: 5,039,935
[45] Date of Patent: Aug. 13, 1991

[54] APPARATUS FOR PARTICLE DETERMINATION IN LIQUID METALS

[75] Inventors: Raynald Hachey, Brassard, Shipshaw; Gaetan Deschenes, Heberville, both of Canada

[73] Assignee: Alcan International Limited, Montreal, Canada

[21] Appl. No.: 471,557

[22] Filed: Jan. 29, 1990

[30] Foreign Application Priority Data

Feb. 3, 1989 [CA] Canada .................................. 590387

[51] Int. Cl.⁵ ...................... G01N 27/00; G01R 27/22
[52] U.S. Cl. ..................................... 324/71.4; 164/41; 266/99
[58] Field of Search ................ 324/71.1, 71.4; 377/10, 377/11, 12; 266/164; 164/4.1

[56] References Cited

U.S. PATENT DOCUMENTS

| | | | |
|---|---|---|---|
| 3,502,973 | 3/1970 | Coulter et al. | 324/71.1 |
| 3,652,427 | 3/1972 | Flood et al. | 324/71.4 |
| 3,987,391 | 10/1976 | Hogg | 377/12 |
| 4,161,690 | 7/1979 | Feier | 324/71.4 |
| 4,278,519 | 7/1981 | Won | 324/71.1 |
| 4,447,883 | 5/1984 | Farrell et al. | 324/71.4 |
| 4,555,662 | 11/1985 | Doutre et al. | 324/71.4 |
| 4,600,880 | 7/1986 | Doutre et al. | 324/71.1 |
| 4,763,065 | 8/1988 | Hachey | 324/71.4 |

Primary Examiner—Kenneth A. Wieder
Assistant Examiner—Maura K. Regan
Attorney, Agent, or Firm—Cooper & Dunham

[57] ABSTRACT

The invention relates to apparatus as disclosed for example in U.S. Pat. Nos. 4,555,662 and 4,600,880 for on-line particle determination in molten metals, wherein a sample of the molten metal is drawn by a vacuum through a calibrated passage in the side-wall of a heat-resistant tube while a current is established through the passage between two electrodes on either side thereof. The passage of non-conducting particles through the orifice produces pulses whose magnitude and rate indicate respectively their size and the number of particles per unit volume. The electrodes and their leads form an interference-receiving antenna so that the wanted test signal, whose signal/noise ratio is inherently low, is subject to interference from neighbouring sources, such as motors, fluorescent lamps and particularly induction furnaces. The invention provides for the production of a cancellation signal to reduce the unwanted interference component in the test signal by means of a cancellation antenna suficiently close to the detector electrodes to receive substantially the same signal, the antenna either feeding the cancellation signal to a differential amplifier also fed with the wanted signal, or being connected in series with the interference antenna. The cancellation antenna can comprise a loop mounted on the head that supports the two electrodes.

7 Claims, 3 Drawing Sheets

APPARATUS FOR PARTICLE DETERMINATION IN LIQUID METALS

FIELD OF THE INVENTION

This invention is concerned with improvements in or relating to apparatus for particle determination in liquid metals, used for the detection and associated measurement of the number, and/or size distribution of particles present in liquid metals.

REVIEW OF THE PRIOR ART

There are disclosed and claimed in U.S. Pat. Nos. 4,555,662 and 4,600,880 a method and apparatus for the on-line detection of the number and size of solid particles in liquid metals, particularly liquid aluminum The apparatus which has been developed is known as the "LIMCA" analyser, and briefly comprises a vessel of suitable heat-resistant, electrically non-cońductive material having a small, precisely-dimensioned bore in a side wall. The vessel is immersed in the liquid metal to be tested and a uniform stream thereof is passed through the bore, usually by means of a vacuum drawn in the vessel interior, while an electric current is established through the stream between two electrodes disposed respectively inside and outside the vessel. The particles of interest are usually non-conductive and the passage of a particle through the bore is therefore accompanied by a decrease in the current to produce a pulse whose magnitude is an indication of the size of the particle. The number of pulses produced while a fixed volume of metal passes through the bore is an indication of the number of particles per unit volume in the metal.

The bore cannot be too small, or it is easily blocked by the larger particles, and small particles passing through a large bore will produce pulses of indeterminate shape and of magnitude little different from that of the background current, which is intrinsically relatively high owing to the high conductivity of liquid metal. It is therefore found iń practice difficult to extract the wanted pulse signals reliably from the background random "noise", since unless considerable care is taken the noise signals may be of about the same order of magnitude as the wanted signals for the smaller particles. To this end the supply current must be carefully filtered and smoothed, the vacuum (or pressure) used to move the metal through the bore must be free of pump-generated pulses, and the entire apparatus must be shielded against outside electromagnetic interference.

Many types of equipment that inevitably are present in an industrial environment may be sources of such interference, such as electric motors, electric welding machines, fluorescent lights, high voltage lines and induction furnaces, the interference either being propagated through the power supply cables, or by radiation through space.

The design and use of filters to reduce or eliminate interference is now a well-developed art, but with this apparatus is made difficult by the relatively low voltage signals characteristic of the particle-indicating pulses (e.g. about 20-300 microvolts), and the fact that the pulse frequencies (corresponding to the number of particles per unit time passing through the passage) are in the range 150-10,000 Hertz, which is of the same order as that of the interfering noise pulses. Shielding can be provided to reflect or absorb the broadcast radiation before it reaches the apparatus, but it is impossible to achieve the ideal shield, consisting of an entirely closed metal box, because of the need for inputs and outputs to and from the box interior; the input and output cables must therefore also be fully shielded, so that effectively they become an extension of the closed box interior. A technique found to be of value is to isolate parts of the test circuit from one another, whenever that is possible, to avoid the formation of local current loops that are particularly receptive of such interference, either by the use of known opto-insulators or with the help of insulation transformers.

A particularly difficult source of interference to deal with is an induction furnace, in that it broadcasts punctual and continuous bursts of strong interference that are particularly easily confused with the required signals, while filters, shields and insulation have limited efficiency in the case of such a source. It is one of the principal virtues of the "Limca" apparatus that it can be used for "on-line" tests to give results in sèconds, compared to prior apparatus which required several hours or even days, but this does dictate that the apparatus is close to the liquid metal source, with the above-described problems if this is a induction furnace.

DEFINITION OF THE INVENTION

It is therefore an object of the invention to provide in such apparatus means for providing an interference cancellation signal that can be used to correct the wanted signal by reduction of as much as possible of the interfering component thereof.

In accordance with the present invention there is provided apparatus for the detection and measurement of particles in liquid metal comprising:

electrically insulating wall means having a passage therein for the passage of molten metal therethrough.;

means for passing molten metal through the passage in the form of a stream thereof;

a pair of test electrodes disposed on opposite sides of the wall means to establish a current path between them through the passage;

test current supply lead means connected respectively to the test electrodes for passing a test current between the two electrodes from a source thereof;

test lead means connected respectively to the pair of electrodes for connection to means for detecting a voltage difference between the test electrodes and changes in the voltage difference resulting from the passage of lesser-conducting particles through the passage and for the consequent production of a corresponding test signal;

the pair of test electrodes constituting at least part of an interference antenna producing an interference signal from incident electric or magnetic interference that is superimposed on the test signal;

a cancellation antenna disposed adjacent the said interference antenna to produce an interference cancellation signal from the said incident interference; and means for adding the interference cancellation signal to the said test and interference signals in opposition to the interference signal to at least reduce its the amplitude.

DESCRIPTION OF THE DRAWINGS

Particular preferred embodiments of the invention will now be described, by way of example, with reference to the accompanying diagrammatic drawings wherein.

DESCRIPTION OF THE PREFERRED EMBODIMENTS

Figure 1:
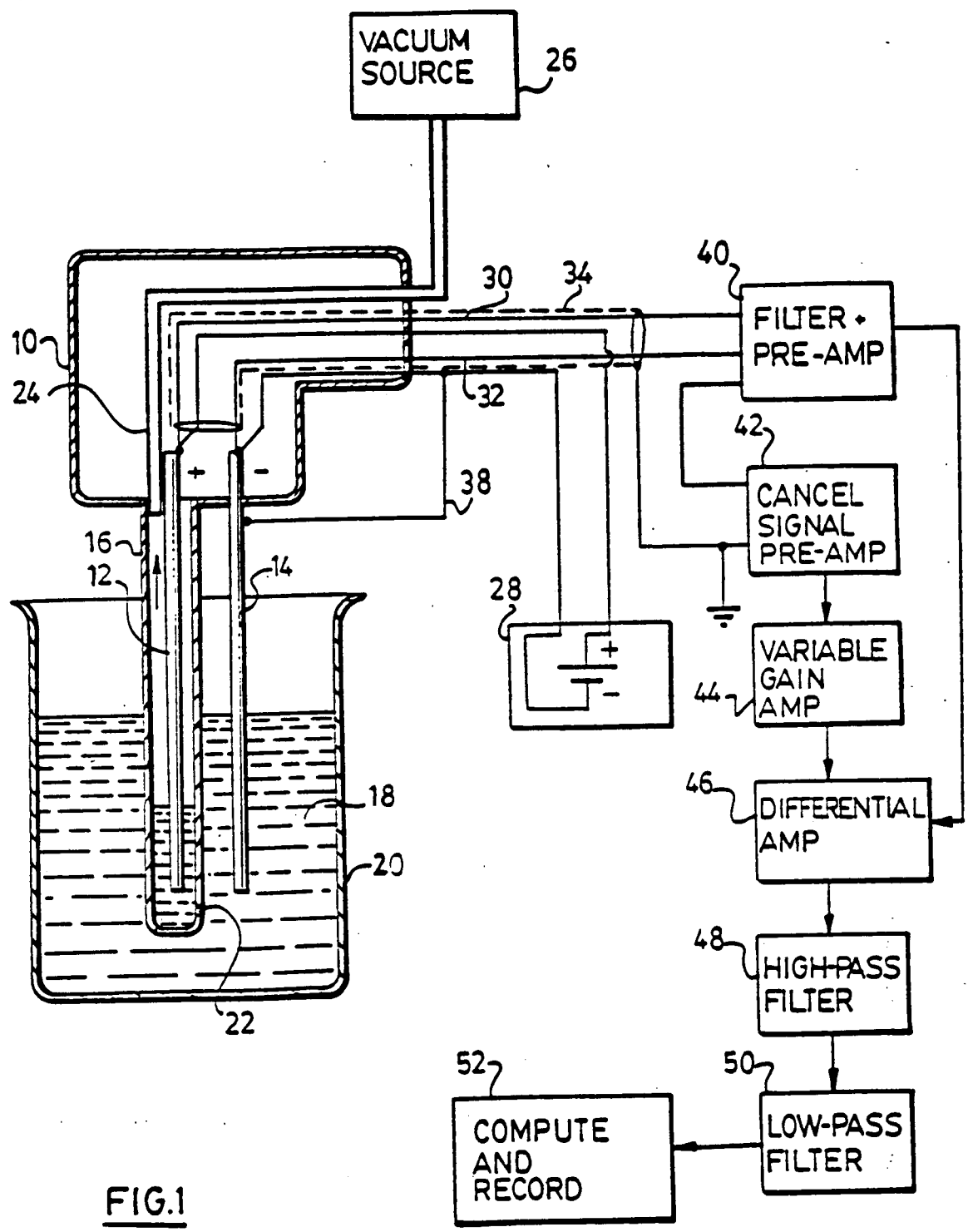
FIG. 1 is a schematic and block diagram of a first embodiment.

The first embodiment of the invention is illustrated applied to a "Limca" (trade name) sampling head 10 comprising two transversely-spaced parallel downwardly-protruding electrodes 12 (positive) and 14 (negative), the positive electrode 12 extending into a sampling tube 16, while the negative electrode 14 extends directly into the molten metal 18 to be examined, which is shown for convenience in illustration as contained in a vessel 20. However, in all of the embodiments any body of molten metal can be tested, such as a flowing stream thereof passing in a transfer trough, and it is one of the advantages of apparatus of the invention that it can rapidly produce useful readings while the metal is flowing. The tube 16 is provided in its side wall facing the negative electrode 14 with an accurately-formed passage 22, through which metal is drawn into the cell formed by the tube by a vacuum established in the cell via an outlet tube 24 by a vacuum source 26, while a relatively heavy direct current, usually of the order of 60 amps, is fed to the electrodes from a D.C. current source 28, usually a heavy-duty rechargeable D.C. battery, via negative and positive leads 30 and 32 respectively. The two leads are enclosed in a shield 34 to reduce pick-up, the shield being grounded and also electrically connected by connection 38 to the negative electrode 14. The signal consisting of the resultant wanted test pulse-containing voltage difference detected between the electrodes 12 and 14 and leads 30, 32 is fed to a circuit 40 comprising in combination a preamplifier (X 100) and high pass filter (150 Hz).

The current-carrying cables 30 and 32 are shielded as effectively as is possible in practice but they, together with the electrodes 12 and 14 (and together with any other associated elements of the apparatus that are operatve to pick up interference) constitute what is defined herein for convenience in terminology as an interference antenna. The effectiveness of this antenna unfortunately cannot easily be reduced without impairing the ease of installation, use and mobility of the measuring head and the connecting cables. The interference antenna inevitably picks up extraneous signals from local sources of noise, and because of the difficulty, if not impossibility, of shielding the two electrodes 12 and 14, is quite efficient as such. In a particular embodiment the electrodes 12 and 14 can measure up to 90 cms (36 inches) in length, are spaced apart about 5 cms.(2 ins.) and are immersed up to 15 cms (6 inches) in the molten metal to result in an electrode loop antenna of effective cross-section about 387 sq.cm (60 sq.in.). This loop antenna is found to be quite highly directional, to the extent that it can even be used to detect the direction of the source or sources of the incident interference. The shielded cable containing the leads 30, 32 can in some embodiments be as long as 7.6 meters (25 feet) and the effective antenna cross-section must also be calculated and added to that of the electrodes.

One of the most difficult sources to deal with is an induction furnace in that it broadcasts electromagnetic interference in or near to the sampling frequency range characteristic of this apparatus (i.e. 200 Hz to 10 kHz), so that it cannot be rejected by a passband or notch filter without adversely affecting the wanted signals. As explained above, a major advantage of this type of apparatus is the ability to use it "on-line", which usually requires its use close to the induction furnace, e.g. within about 15 meters (45 feet), where it is well within the broadcast area of the interference. Shields and insulation are of limited efficiency in the presence of such electromagnetic interference and so close to its source, and a signal pre-amplifier cannot be located to receive the wanted signals without also receiving the unwanted signals.

In accordance with the invention, in this first embodiment an additional or supplementary signal cancellation loop antenna is formed by the negative current-carrying cable wire 32 and the shield 34, the loop being completed by the connection 38 between the shield and the electrode 14. It will be understood that the loop could also be formed between the positive current-carrying cable 30 and the shield, but persons skilled in this art would normally prefer to use the negative cable for this purpose for convenience in designing and installing the associated circuit. This cancellation loop antenna is subjected to substantially the same interference field, and has an effective cross-section of about the same order of magnitude as the interference antenna. It is therefore possible to obtain from it an interference cancellation signal of about the same order of magnitude as the unwanted interference signal, and having a sufficiently similar characteristic or "envelope" to be able to provide useful cancellation of the interference in the wanted test signal if combined therewith out of phase by ninety degrees.

This cancellation signal is therefore supplied to a cancellation signal pre-amplifier 42 of substantially the same gain as the amplifier 40, the output of amplifier 42 being fed to a variable gain amplifier 44, the output of which is in turn fed to a differential amplifier 46, while the output of amplifier 40 is the other input to the amplifier 46. The gain of amplifier 44 is adjusted until the cancellation signal from the cancellation antenna is sufficient to just cancel the interfering signal component in the output signal from the amplifier 40, and the resultant corrected pulse-containing wanted signal output is fed through a passband filter constituted by successive high and low pass filters 48 and 50, and thence to a computation and recording apparatus 52, as described in detail in the said U.S. Pat. Nos. 4,555,662 and 4,600,880, the disclosures of which are incorporated herein by this reference. This recording apparatus produces a permanent visible record indicating the number of particles per unit volume of metal and their relative size distribution.

Figure 2:
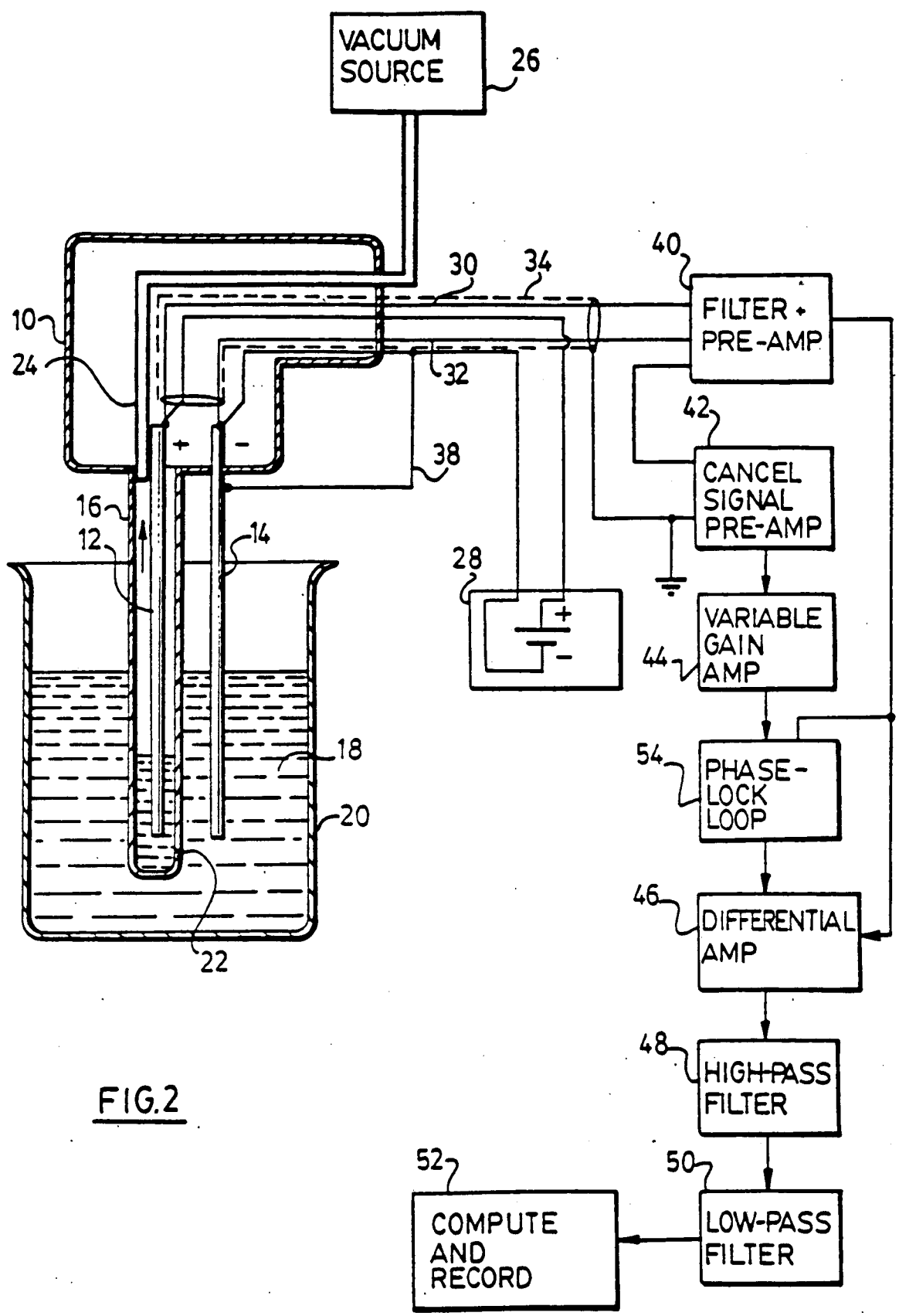
FIG. 2 is a similar diagram of a second embodiment.

A second embodiment is illustrated by FIG. 2 in which a phase-lock loop circuit 54 is interposed between the variable gain amplifier 44 and the differential amplifier 46 and is fed with the two signals. This circuit permits the relative phase of the two signals to be maintained constant, so that there will not be any output signal variation due to phase differences.

Figure 3:
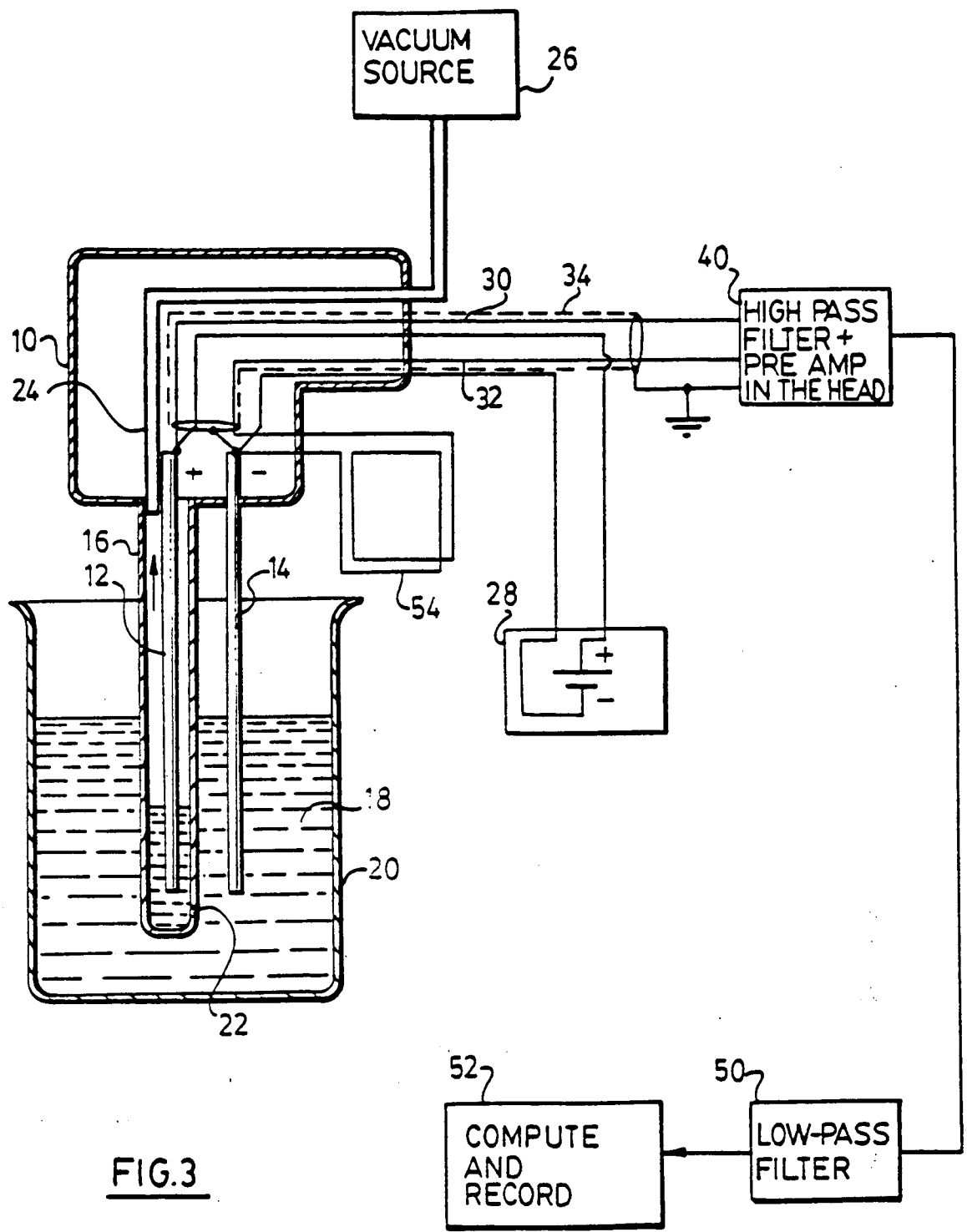
FIG. 3 is a similar diagram of a third embodiment.

A system of this kind is most effective if permanently installed, since otherwise it presents some difficulties of operation, in that the relatively long cables 30 and 32 must then be flexible and any movement during operation will usually change the effective cross-sections of both the interference and cancellation antennae. In the embodiment of FIG. 3 the cancellation antenna 54 instead consists of a sufficient number of turns of fine wire (e.g. #20) mounted closely adjacent to the head 10, preferably on the head 10, in any convenient manner. The antenna 54 is connected between the negative electrode 14 and the electrode lead 32, so that the interference cancellation signal it produces is directly electrically opposed to the test and interference signals. Since the two signals are opposed in this manner only a single amplifier will be required and the need for the differential amplifier 46 is eliminated. The antenna 54 is installed so that the plane of its loop is parallel to that of the loop formed by the electrodes 12 and 14 and, since it is so closely physically associated with the head, it is subjected to the same interfering field. Since the two loops always remain in the same position and orientation relative to one another and to the head 10 in the interfering field they always produce corresponding signals. Thus once the loop 54 is adjusted in effective cross-section area for the particular apparatus head 10, e.g. by physically changing the relative length and width of the turns, the apparatus will require only adjustments that can be accomplished electrically.

The opportunity is also taken of eliminating, or at least reducing as much as possible, the loop antenna effect of the cables 30 and 32 by incorporating the high pass filter 48 of the prior circuits in with the single preamplifier 40, and by connecting the resultant amplifier 40 directly to the electrodes 12 and 14 and mounting it within the head, the greatly amplified signal that is fed to the low pass filter 50 being less sensitive to interference pick-up.

We claim:

1. Apparatus for the detection and measurement of particles in liquid metal comprising:
   electrically insulating wall means having a passage therein for the passage of molten metal therethrough;
   means for passing molten metal through the passage in the form of a stream thereof;
   a pair of test electrodes disposed on opposite sides of the wall means to establish a current path between them through the passage and constituting at least part of an interference antenna producing an interference signal from incident electric or magnetic interference;
   test current supply lead means connected respectively to the test electrodes for passing a test current between the two electrodes from a source thereof;
   test lead means connected respectively to the pair of electrodes for connection to means for detecting the voltage difference between the test electrodes and changes in the voltage difference resulting from the passage of lesser-conducting particles through the passage and for the consequent production of a corresponding test signal to which the interference signal is added;
   a cancellation antenna disposed adjacent the said interference antenna to produce an interference cancellation signal from the said incident interference;
   and means for adding the interference cancellation signal to the said added test and interference signals in opposition to the interference signal to at least reduce its amplitude.

2. Apparatus as claimed in claim 1, wherein the said test and interference signals are fed to a differential amplifier as one input thereof, and the said interference cancellation signal is fed to the differential amplifier as another input thereof, the output of the amplifier being the difference between the two inputs.

3. Apparatus as claimed in claim 2, and including a variable gain amplifier connected between the interference antenna and the corresponding differential amplifier input to adjust the amplitude of the interference cancellation signal.

4. Apparatus as claimed in claim 1, wherein the said interference antenna also comprises a pair of test lead cables constituting the test lead means which connect the test electrodes to the current source, and wherein the said cancellation antenna is constituted by one of the test lead cables and a shield enclosing the pair of test lead cables.

5. Apparatus as claimed in claim 1, wherein the pair of test electrodes are supported by support means and said cancellation antenna is constituted by a loop antenna mounted on the support means.

6. Apparatus as claimed in claim 1, wherein the pair of test electrodes are supported by support means and said cancellation antenna is constituted by a loop antenna mounted on the support means with its plane parallel to that of the interference antenna.

7. Apparatus as claimed in claim 1, wherein the pair of test electrodes are supported by support means and said cancellation antenna is constituted by a cancellation loop antenna mounted on the support means with its plane parallel to that of the interference antenna, the cancellation loop antenna being connected in series with the interference antenna so that its cancellation signal is opposed to that of the interference signal.

* * * * *